(12) United States Patent
Parker

(10) Patent No.: US 7,047,656 B1
(45) Date of Patent: May 23, 2006

(54) TOOTH CIRCUMFERENCE MEASURING DEVICE

(76) Inventor: Richard Ross Parker, 315 Arbolada Dr., Arcadia, CA (US) 91006

( * ) Notice: Subject to any disclaimer, the term of this patent is extended or adjusted under 35 U.S.C. 154(b) by 0 days.

(21) Appl. No.: 10/835,126

(22) Filed: Apr. 29, 2004

Related U.S. Application Data

(60) Provisional application No. 60/466,989, filed on May 1, 2003.

(51) Int. Cl.
*G01B 3/10* (2006.01)

(52) U.S. Cl. ........................ 33/514; 33/514.1; 33/555.4

(58) Field of Classification Search ................ 33/514, 33/511, 512, 513, 514.1, 755, 756, 555.1, 33/555.4; 433/72
See application file for complete search history.

(56) References Cited

U.S. PATENT DOCUMENTS

| | | | |
|---|---|---|---|
| 855,875 A | 6/1907 | Bode | |
| 984,040 A | 2/1911 | Siverling | |
| 1,233,131 A | * 7/1917 | Schwartz | ...................... 33/514 |
| 1,448,222 A | 3/1923 | Johnston et al. | |
| 1,887,220 A | 11/1932 | Stuckeman | |
| 2,231,121 A | 2/1941 | Hormann | |
| 3,583,071 A | * 6/1971 | Bitter | ........................... 33/513 |
| 3,744,140 A | * 7/1973 | Kyrk | ......................... 33/514.1 |
| 3,839,801 A | 10/1974 | Tappe | |
| 3,889,382 A | 6/1975 | Husted et al. | |
| 5,212,871 A | 5/1993 | Luccarelli | |
| 5,529,489 A | 6/1996 | Herrera | |

* cited by examiner

*Primary Examiner*—Christopher W. Fulton
(74) *Attorney, Agent, or Firm*—Marsh Fischmann & Breyfogle LLP

(57) ABSTRACT

A tooth circumference measuring device is disclosed that device provides a strap that is placed around a dental patient's tooth and retracted into an at least generally conformal relationship (i.e., snuggly fit around the tooth) using a strap adjusting mechanism. The strap is operatively interconnected to a gage such that when the strap is secured about the tooth with a predetermined amount of tension, the gage indicates the circumference of that tooth. In one embodiment, the strap adjusting mechanism includes a reel that is interconnected to the strap. Upon rotation of the reel, a first portion of the strap is wound or unwound about a perimeter of the reel such that a second portion of the strap disposed about a tooth may be tensioned or loosened. In a further embodiment, the strap adjusting mechanism is operative to provide a consistent tension between measurements.

33 Claims, 11 Drawing Sheets

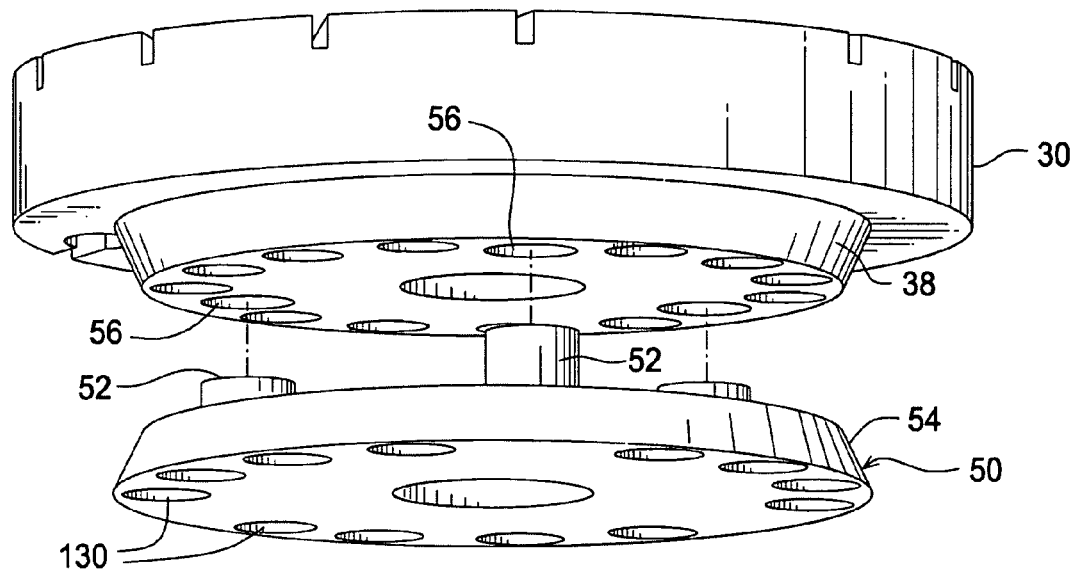
FIG.8
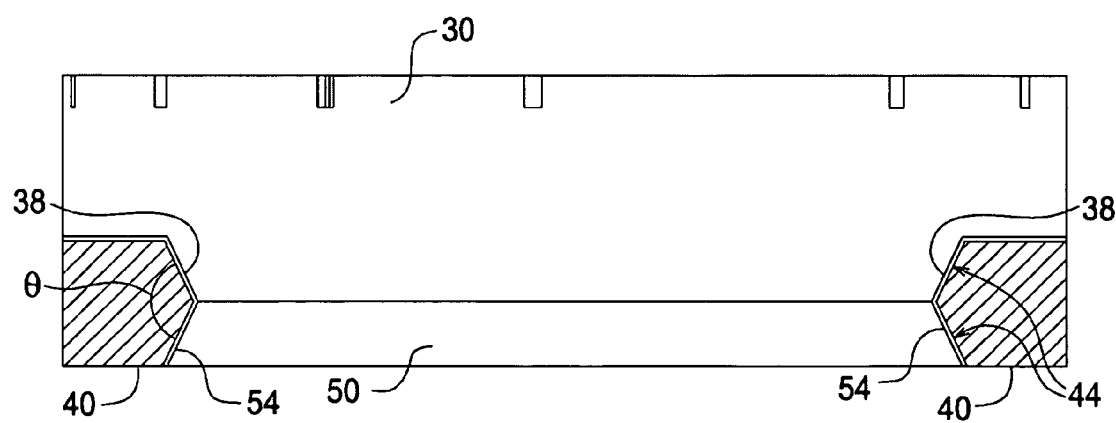

TOOTH CIRCUMFERENCE MEASURING DEVICE

CROSS REFERENCE TO RELATED APPLICATIONS

This application claims priority under 35 U.S.C. §119 to U.S. Provisional Application No. 60/466,989 entitled: "Tooth Circumference Measuring Device," having a filing date of May 1, 2003; the contents of which are incorporated by reference herein as if set forth in full.

FIELD OF THE INVENTION

The present invention relates to a device utilized to measure the circumference of a patient's teeth for purposes of orthodontic sizing and analysis.

BACKGROUND

In a number of dental and orthodontic procedures, hardware is fitted on or around a tooth of a patient. For instance, orthodontic bands consisting of a thin strip of steel may be placed about the perimeter of a tooth and cemented into place. Accordingly, additional hardware (e.g., brackets) may be attached to these bands.

As will be appreciated, it is desirable for dental hardware placed on or around a tooth to conform with that tooth in order to achieve a secure interconnection, as well as for reasons of patient comfort. In this regard, dental hardware such as crowns and bands come in a variety of sizes to accommodate differently sized teeth, as well as to accommodate multiple classes of teeth (e.g., incisors, bicuspids, molars, and corresponding groups of deciduous teeth). Fitting of such hardware to the teeth of a patient has typically been performed via a trial and error approach where a dental technician examines a given tooth and estimates the appropriate size for the hardware. Due to the irregular shape of many teeth, such estimation is often an inefficient method for selecting hardware. For instance, when fitting bands, a technician may have to place multiple bands about a single tooth in order to identify hardware of the correct size. In addition to increasing the time required for fitting, this requires re-sterilization and restocking of tested, but incorrectly sized hardware. Accordingly, a device for accurately and easily measuring the circumference of a tooth would be desirable.

SUMMARY

An object of the present invention is to provide a device for accurately measuring the circumference of one or more of a patient's teeth.

Another object of the present invention is to provide a tooth circumference-measuring device that accommodates multiple classes of teeth (e.g., incisors, bicuspids, molars, and corresponding groups of deciduous teeth).

Another object of the present invention is to provide a tooth circumference-measuring device having a simplified construction.

Another object of the present invention is to provide a tooth circumference-measuring device that may be cold sterilized.

Another object is to provide a tooth circumference measuring device having a measuring strap that is readily replaceable.

Another object is to provide a tooth circumference measuring device that facilitates measuring strap placement about a patient's tooth.

These and additional objectives are indeed realized by the tooth circumference measuring device of the present invention. As presented, the device provides a strap that is placed around the patient's tooth and retracted into an at least generally conformal relationship (i.e., snuggly fit around the tooth) using a strap adjusting mechanism. The strap is operatively interconnected to a gage such that when the strap is secured about the tooth with a predetermined amount of tension, the gage indicates the circumference of that tooth.

In a first aspect, the device includes a measuring strap that is anchored to and rotatable with a reel, which is rotatively coupled to the body of the device. More particularly, the measuring strap includes a first portion that is interconnected to the reel, a second portion that is anchored to the body of the device, and a loop portion that projects through a tip section of the device and forms a loop. The strap may be wound or unwound around an outside perimeter of the reel such that the loop may be contracted and/or expanded. Typically, the device will further include a gage and an indicator that is operatively connected to the strap to identify movement of the strap. For instance, the indicator may be attached to the reel such that it rotates with the reel in conjunction with the strap being wound/unwound about the reel. In any case, the position of the indicator relative to the gage will be indicative of the size of the loop and, hence, the circumference of a tooth that may be disposed within that loop.

Various refinements exist of the features noted in relation to the first aspect of the present invention. Further features may also be incorporated in the first aspect of the present invention as well. These refinements and additional features may exist individually or in any combination. For instance, the reel may be any structure rotatively coupled to the device. What is important is that the reel is operative to wind and unwind a portion of the strap in order to adjust the size of the loop. Likewise, the body of the device may be of any appropriate shape. However, in one particular embodiment, the device will include an elongated section designed for positioning within a mouth of a patient. Accordingly, the loop may project through a tip of this elongated section, which may be conformed to facilitate a spreading apart of the measuring strap.

As noted, a first portion of the measuring strap is interconnected to the reel while a second portion of the strap is interconnected (e.g., anchored) relative to the body of the device. However, the strap may be removeably interconnected to the reel and body such that the strap may be removed and/or replaced, for example, between uses on different patients and/or to allow for sterilization of the same. In this regard, a mechanism for interconnecting one or both ends of the strap to the device may be required. In one embodiment, mandrels are incorporated into the strap that fit into keyways and pockets formed within the reel and body of the device. In this regard, the mandrel of the strap may be inserted into a pocket on the reel and the strap may be routed through the keyway or channel extending from the pocket, and which has a reduced size (e.g., width) in comparison with the pocket. However, it will be appreciated that other mechanisms (e.g., clamps, and hooks that engage conforming holes through the strap) may be utilized to interconnect the strap to the reel and/or body of the device.

The measuring strap may be formed from any appropriate material that allows the strap to be positioned around and conformed to the perimeter of a tooth of a patient. Preferably, the strap will be formed from a material that is resistant to stretching. Such materials include, without limitation, metals, metal alloys, composite materials (e.g., carbon fibers or aramid fibers) and/or plastics. When metals or metal alloys are utilized, it is preferable that they have a modulus of elasticity of at least about $28 \times 10^6$ psi. In any case, the length, width, and thickness of the strap may be selected for desired properties. For instance, the thickness of the strap may be selected to provide a strap having a desired flexibility. In one embodiment, the strap has a width of about 0.15 inches and a thickness of about 0.0025 inches. However, this is not a requirement.

The gage provides an indication of the size of the loop extending from the tooth-measuring device. In this regard, an indicator for the gage may be interconnected to the strap, the reel, or to a strap adjuster that is operative to move the strap. In one application, such an adjuster may be operative to turn the reel to wind/unwind the strap about the reel. The gage may include any appropriate mechanism for indicating the size of the loop extending beyond the tooth-measuring device. In this regard, the gage may include a linear or radial face plate having a number of gradations that are indicative of the size of the circumference of the loop extending beyond the device. As will be appreciated, these gradations may conform to standard sizes (e.g., in inches or centimeters), or may correspond with manufacturer-specific sizes. For example, different manufacturers may utilize different sizing indicia for their hardware. In this regard, gradations on the gage may correspond to the measuring system of specific manufacturers.

The gage or a faceplate of the gage may also be removable from the device such that different gages having different gradations may be utilized. In this regard, different classes of teeth, or, teeth of different sizes (e.g., adult and children) may be measured using the same device. Irrespective of the gradations utilized by the gage, it may be desirable that the gage account for a statistical majority of the teeth it is designed to measure.

To provide accurate measurement, the gage may have to be calibrated. In this regard, a standard having a known diameter may be placed in the loop and the strap may be tightened to conform the loop about that standard. While so disposed, an indicator associated with the gage may be disposed relative to a calibration point (e.g., on the gage) associated with the standard. In this regard, an indicator may be moved to the calibration point, or, one or both ends of the strap may be adjusted (i.e., tensioned or loosened) in order to move the adjustor to the calibration point. As will be appreciated, utilization of different gages may require the utilization of different standards for calibration.

When utilized, the strap adjusting mechanism may be any mechanism that is operative to turn the reel such that the measuring strap is wound or unwound around the outside perimeter of the reel. In this regard, the strap adjusting mechanism may be fixedly interconnected to the reel (e.g., such as a knob or lever), or, may be otherwise operative to turn the wheel. For instance, in one embodiment, the strap adjusting mechanism is disposed in a frictional relationship with the reel. That is, the strap adjusting mechanism is operative to turn the reel until the tension in the strap exceeds a frictional force between the strap adjusting mechanism and the reel. Once such a tension in the measuring strap is achieved, additional tensioning of the strap adjusting mechanism will not further turn the reel. As will be appreciated, such a system may allow for applying a consistent tension to teeth disposed within the loop of the measuring strap such that consistent measurement may be made between different teeth. In another embodiment, the lever is fixedly interconnected to the reel such that turning the lever rotates the reel and hence winds or unwinds the measuring strap. In this embodiment, the lever may also be utilized as an indicator for a gage. That is, the same device that may be used to move the reel may also be used as an indicator in relation to a gage for indicating tooth size.

According to a second aspect of the present invention, a tooth-measuring device is provided that allows for cold sterilization by immersion in a sterilant. In this regard, the measuring device has an open design that reduces the potential for sterilant from becoming trapped within enclosed portions of the device. The device includes a body having a tip section, a strap adjusting mechanism moveably interconnected to a body, and a measuring strap extending from the strap adjusting mechanism through the tip section and forming a loop. The measuring strap is disposed within a concave channel formed within the body that extends from the adjusting mechanism through the tip section of the body. This concave channel is open to the surface of the body over at least substantially the entire length of the channel. In this regard, the strap may be easily removed from the tooth-measuring device. Further, as there are no enclosures such as tubes, sterilant is less likely to become trapped within the device during cold sterilization.

Typically, the channel will have a substantially U-shaped cross section and will be sized in a manner to maintain the strap in an upright position. Although the channel is open over at least substantially its entire length, it may utilize one or more clips or other retainers to maintain the measuring strap therein during use. Preferably, such retainers may be removed during sterilization of the device.

According to a third aspect of the present invention, a tooth measuring device is provided that allows the measuring strap to be tightened repeatedly to a predetermined setting. The device includes a body having a tip section, a reel rotatably coupled to the body, a measuring strap comprising a first portion anchored to the reel, a second portion anchored to the body, and a loop disposed beyond the tip section. The device further includes a strap adjuster mounted on the reel, wherein a frictional interface between the strap adjuster and the reel allows the reel to move along with the strap adjuster when a force exerted on the reel by the measuring strap is less than a predetermined amount, and wherein the reel remains stationary during movement of the strap adjuster when a force being exerted on the reel by the measuring strap is greater than that predetermined amount. In this embodiment, upon achieving a given tension in the strap, the frictional interface between the reel and the strap adjuster will slip, allowing for consistent strap tension between measurements. As will be appreciated, consistent tension in the measuring strap between measurements allows for increased consistency in circumference measurements. That is, measuring differences/errors introduced by differences in individual technician strength and/or other user-specific ergonomics (e.g., tension estimation) may be substantially reduced or eliminated.

Various refinements exist of the features noted in relation to the third aspect of the present invention. Further features may also be incorporated into the third aspect of the invention as well. These refinements and additional features may exist individually or in any combination. For instance, the device may include a fastener for attaching the strap adjuster to the reel. This fastener may allow for selectively adjusting a compressive force between the strap adjuster and the reel, thereby adjusting the force required to initiate slippage between the strap adjuster and the reel. Furthermore, it will be appreciated that the contact surfaces between the strap adjuster and the reel may be sized and/or finished to enhance or reduce the frictional contact between these members.

According to a fourth aspect of the present invention, a tooth circumference measuring device having a simplified construction is provided. The device includes a body having a tip section, a measuring strap comprising a loop disposed beyond the tip section, and a lever operatively interconnected with the measuring strap for moving the measuring strap from a first position to a second position, and a gage. In this simplified embodiment, the position of the lever relative to the gage is indicative of the size of the loop and hence a tooth disposed within that loop.

Various refinements exist of the features noted in relation to the fourth aspect of the present invention. Further features may also be incorporated into the fourth aspect of the invention as well. These refinements and additional features may exist individually or in any combination. For instance, the lever may be directly interconnected to the measuring strap, or may be interconnected to another member that is interconnected to the measuring strap. What is important is that the lever is at least operative to move the strap from a first position to a second position.

In one embodiment, the lever is interconnected to a reel such that the reel and lever move about a common point (i.e., axis). In this embodiment, the strap may be anchored to the reel at a first distance (i.e., radius) from the axis and the gage (e.g., a radial gage) may be located at a second distance (i.e., radius) from the axis that is greater than the first distance. Accordingly, an angular rotation of the reel will result in a movement of the strap over a first length (i.e., arc) and a like angular movement of the lever. Accordingly, the portion of the lever disposed relative to the gage will move over a second larger length (i.e. arc). As will be appreciated, this allows for enhancing the distance between gradations on the gage such that the gage may be more easily read.

According to a further aspect of the present invention, a device for measuring the circumference of a tooth is provided that allows for quickly calibrating the device. Again, the device includes a body and a measuring strap having a first portion, a second portion, and a loop portion between the first and second portion that is disposed beyond the tip section of the device. A strap adjuster moveable relative to the body is interconnected with a first portion of the measuring strap and a calibrator moveable relative to the body is connected to a second portion of the measuring strap. This calibrator is moveable relative to the body so as to change a position of the second portion of the measuring strap. In this regard, the first portion of the measuring strap may be positioned at a known location (e.g., a calibration point) and the calibrator may be moved to tension or loosen the strap such that it the loop is conformal about a standard having a known size.

BRIEF DESCRIPTION OF THE DRAWINGS

FIG. 3b shows an enlarged, perspective view of the end of the measuring strap shown in FIG. 3a.

FIG. 6 shows a perspective view of a reel from the tooth circumference measuring device of FIG. 1 that is utilized to engage one end of the measuring strap shown in FIG. 3a.

FIG. 8 shows a perspective view of two components of the calibration mechanism of FIG. 7.

FIG. 8a shows a cross-sectional view of three components of the calibration mechanism of FIG. 7.

DETAILED DESCRIPTION

The present invention is directed to a tooth circumference measuring device for use in measuring the circumference of a tooth such that an orthodontic band or a crown of appropriate size may be selected for attachment to that tooth. As will be appreciated, this may substantially reduce time consuming trial and error band/crown selection, as well as result in a selection of a band/crown better fitted to a patient's tooth. To measure a tooth circumference, the tooth circumference measuring device provides a strap that is placed around the tooth and retracted into an at least generally conformal relationship (i.e., a snug fit around the tooth). The strap is operatively interconnected to a gage such that when the strap is secured about the tooth, the gage indicates the circumference of that tooth. Accordingly, an appropriately sized orthodontic band may be selected. Furthermore, as will be discussed herein, the tooth circumference measuring device is operative to measure the circumference of different classes of teeth (i.e., molars, bicuspids, and incisors). In this regard, a single instrument is provided that is able to effectively measure all of a patient's teeth for orthodontic sizing and analysis. Though discussed herein as being primarily directed toward measuring the circumference of a patient's teeth, it will be appreciated that the device may also be utilized for related dental purposes, such as sizing temporary pedodontic crowns.

Figure 1:
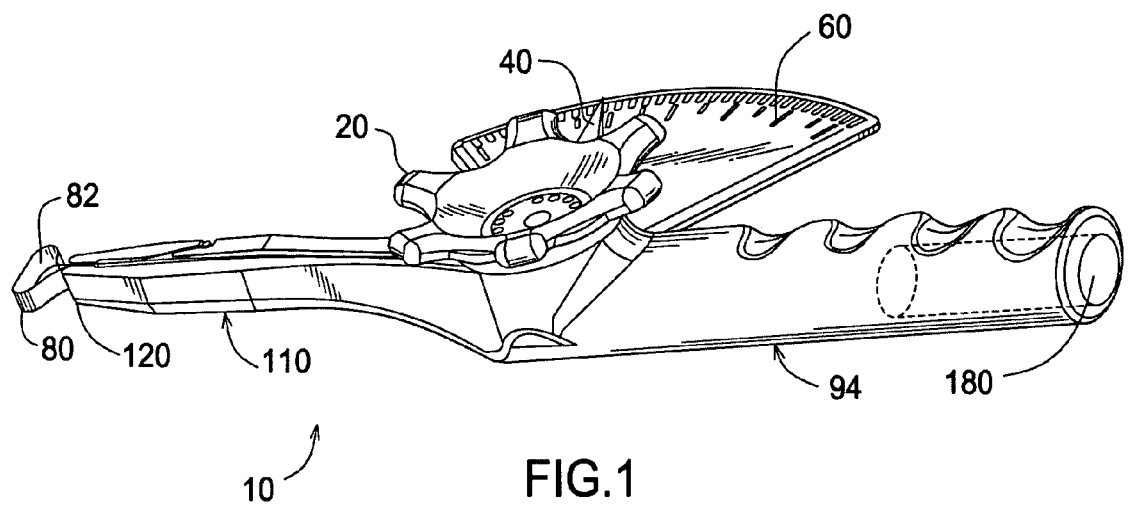
FIG. 1 shows a perspective view of a first embodiment of a tooth circumference measuring device.
Figure 1A:
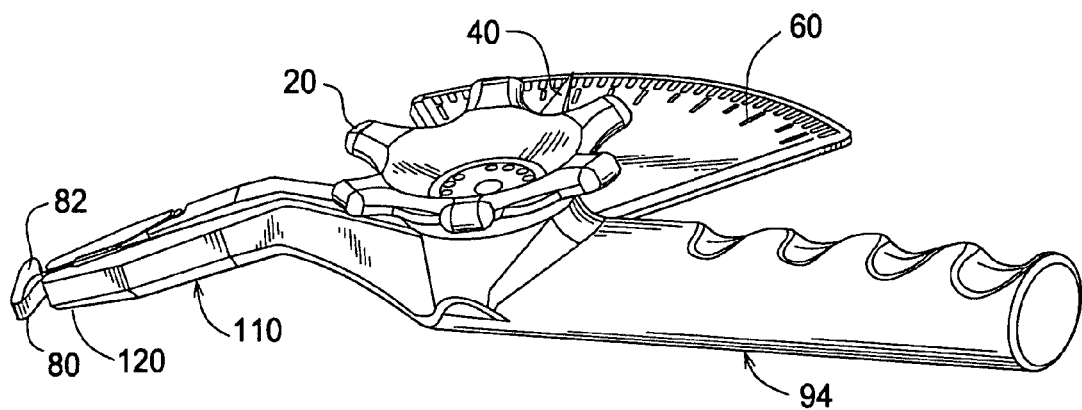
FIG. 1a shows a perspective view of a second embodiment of a tooth circumference measuring device.

FIG. 1 shows a perspective view of one embodiment of a tooth circumference measuring device 10 (hereinafter "device" 10). As shown, the device 10 generally includes a handle 94 for use in positioning/manipulating the device 10, an elongated neck section 110 opposite of the handle 94 and that is disposable in a patient's mouth (the handle 94 and elongated neck section 110 collectively defining a body), a tension control, strap adjuster, or trigger wheel 20 of a tensioning or strap adjusting mechanism, and a gage 60. The handle 94 is located relative to the trigger wheel 20 such that a user may turn the trigger wheel 20 with the thumb of the same hand that holds the handle 94. That is, the device 94 may be operated using a single hand. In the illustrated embodiment, the handle 94 and the neck section 110 are of one-piece construction (e.g., a molded part), although the handle 94 and neck section 110 could be separately formed and appropriately attached. The neck section 110 is a narrow, elongated member that facilitates the measurement of a patient's rearward teeth (i.e., molars). In this regard, the narrow, elongated neck section 110 may be disposed into a patient's mouth. Specifically, it has been found that the elongated neck 110 is particularly useful for measuring the circumference of upper posterior teeth where the technician comes in across the mouth and measure the circumference from the lingual (inside) surface of those upper teeth. As shown, the neck section 110 is substantially aligned with a longitudinal axis of the device 10. However, it will be appreciated that the neck section 110 may alternatively be angled to allow better access to the rearward teeth of a patient (e.g., disposed at an appropriate angle relative to the length dimension or longitudinal extent of the handle 94, as schematically depicted in FIG. 1A).

Protruding from a tip 120 of the device 10 is a measuring strap 80, which forms a loop 82 for placement around a patient tooth. The loop 82 may be expanded or contracted by turning the trigger wheel 20, which controls a tensioning mechanism 18 of the device 10 as will be discussed in more detail below, for instance in relation to FIG. 2. Generally, one end of the strap 80 is interconnected to the tensioning mechanism 18 such that the strap 80 may be adjusted by rotation of the trigger wheel 20. An indicator needle 40 moves with a friction adjustable relationship with trigger wheel 20 associated with the trigger wheel 20 moves relative to the gage 60 during operation of the device 10—more specifically during rotation of the trigger wheel 20. The position of the needle 40 on the gage 60 indicates the size of the loop 82 extending beyond the tip 120 of the device 10 and, hence, the circumference of a tooth disposed within the loop 82.

Figure 2:
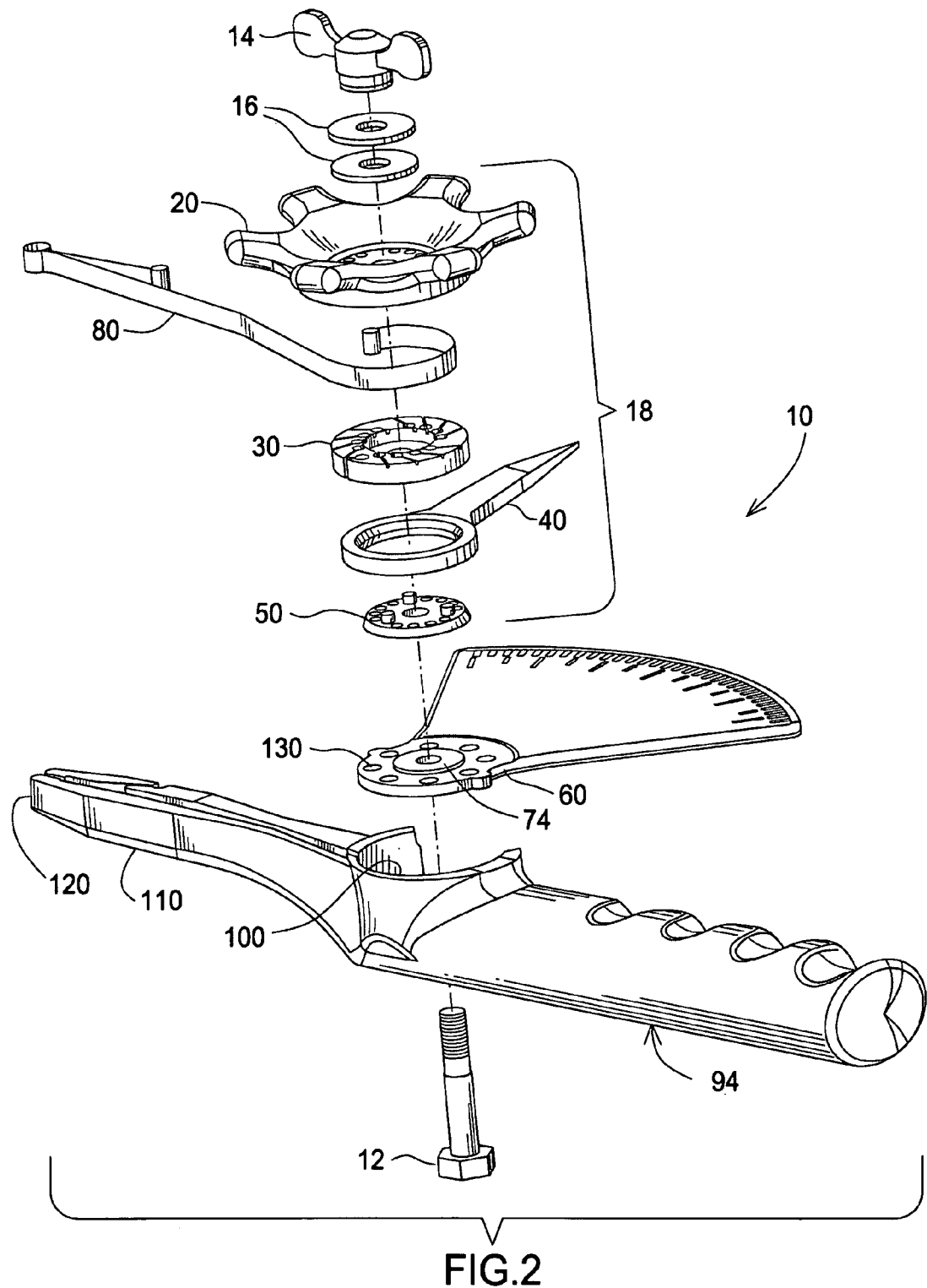
FIG. 2 shows an exploded, perspective view of the tooth circumference measuring device of FIG. 1.

FIG. 2 shows an exploded view of the device 10. Between the handle 94 and neck section 110, the device 10 includes a socket 100 that receives and houses the tensioning mechanism 18 and gage 60. The tensioning mechanism 18 generally includes: the trigger wheel 20; a reel 30 for interconnection with one end of the measuring strap 80; the indicator needle 40; and a lower needle mandrel 50 for holding the indicator needle 40 relative to the reel 30. Upon assembly, these components are appropriately aligned, wherein a bolt 12 or other appropriate fastener extends through an aperture of each of these components. In this regard, the bolt 12 in effect acts as a spindle about which the tensioning mechanism 18 is operative to turn/rotate for tensioning/loosening the measuring strap 80. Stated another way, rotation of the tensioning mechanism 18 at least attempts to change the size of the loop 82 of the tensioning strap 80 that protrudes beyond the tip 120 of the neck section 110. Generally, the trigger wheel 20, the reel 30, the indicator needle 40, and the lower needle mandrel 50 will rotate together relative to the gage 60 until the desired tension is realized. Thereafter, further rotation of the trigger wheel 20 will not cause any further rotation of the indicator needle 40 as a result of the trigger wheel 20 slipping on the reel 30.

The bolt 12 extends through a bottom surface of the device 10. To allow easy assembly and disassembly of the device 10, the head of the bolt 12 is received into a counter sunk hexagonal recess (not shown) on the bottom surface of the device 10 opposite the socket 100. This allows a nut 14 to be tightened onto the bolt 12 without utilizing a wrench to hold the bolt 12. As shown, wing nut 14 is utilized to secure the tensioning mechanism 18 about the bolt 12 within the socket 100. As will be appreciated, utilization of the countersunk recess and a wingnut 14 allows for hand assembly/disassembly of the device 10. However, this is not a requirement in that any appropriate way of interconnecting the tensioning mechanism 18 may be utilized. Of note, an appropriate number of Belleville or spring washers 16 are utilized to assemble the tensioning mechanism 18 of the device 10 (two shown in the illustrated embodiment). As will be appreciated, these washers 16 are slightly conical such that they form a spring when axially loaded/compressed. Upon tightening of the wingnut 14, these spring washers 16 maintain a substantially constant pressure on the tensioning mechanism 18 during operation of the device 10. This allows for controlling the tension applied by the measuring strap 80 to a patient's tooth. More specifically, the resistance to rotation of the trigger wheel 20 relative to reel 30 may be adjusted by the degree to which the wingnut 14 is threaded onto the bolt 12, which in turn has an effect on the spring force generated/applied by the spring washers 16.

Figure 3A:
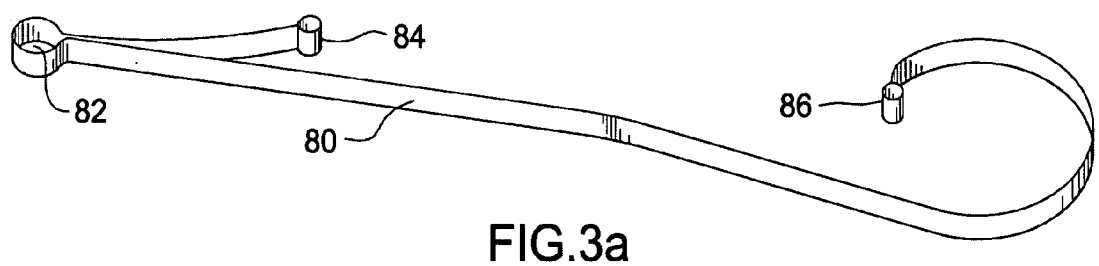
FIG. 3a shows a perspective view of a measuring strap utilized with the tooth circumference measuring device of FIG. 1.

FIG. 3a shows one embodiment of a measuring strap 80 that may be utilized with the device 10. In the present embodiment, the measuring strap 80 is formed from work hardened spring tempered stainless steel that provides a strap 80 that is resistant to stretching, with a modulus of elasticity (i.e., Young's modulus) of at least about $28 \times 10^6$ psi. In this regard, a plurality of teeth may be individually measured without calibrating the device 10 between measurements. Furthermore, the spring steel provides a strap 80 that is flexible enough to substantially conform to a patient's tooth upon tensioning such that accurate tooth circumference measurements may be made. However, it will be noted that other materials such as chromium cobalt alloys and high modulus composite materials may also be utilized to form the strap 80. Any appropriate material may be used for the strap 80.

Figure 3B:
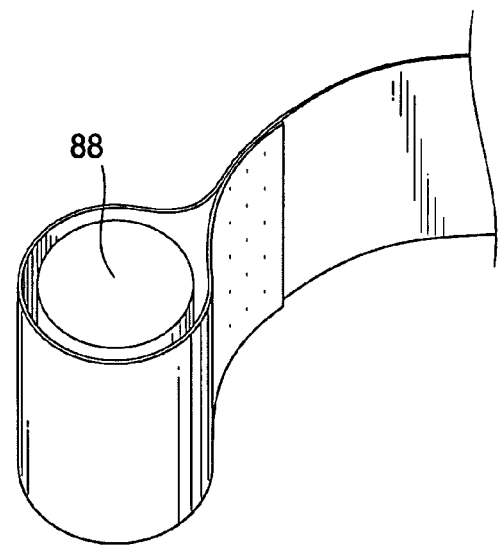

In the present embodiment, the strap 80 has a width of about 0.15 inches and a thickness of about 0.0025 inches. Furthermore, the two opposite ends 84, 86 of the strap 80 are each formed about a mandrel 88, (see FIG. 3b) such that they may be retained within pockets formed in the neck section 110 and reel 30 of the device 10, as will be more fully discussed herein. As shown, each end 84, 86 of the strap 80 is formed by wrapping a portion of the strap 80 around the mandrel 88 and resistance welding the strap 80 to itself in one or more places. Other ways of mounting the strap 80 on the mandrel 88 may be utilized.

Figure 4:
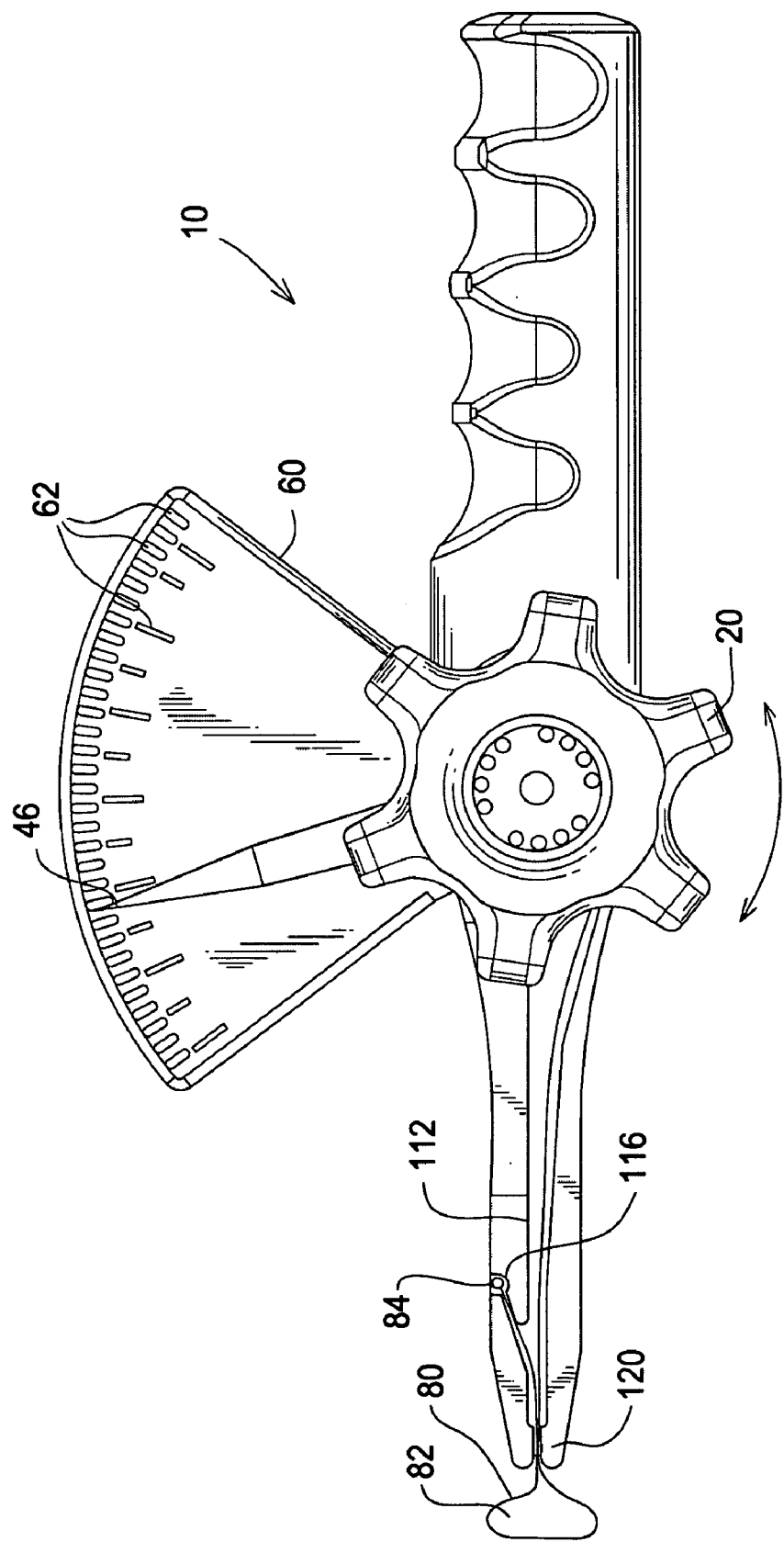
FIG. 4 shows a plan view of the tooth circumference measuring device of FIG. 1.
Figure 5:
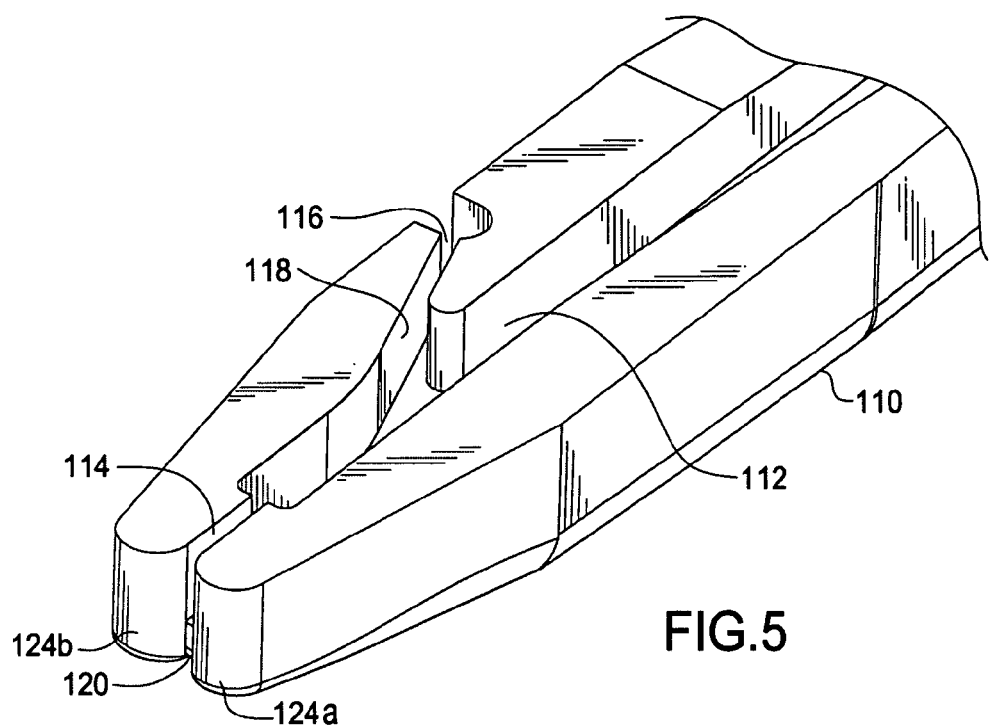
FIG. 5 shows a close up perspective view of the forward end of the tooth circumference measuring device of FIG. 1.

FIGS. 4 and 5 show a top where the measuring strap 80 is seated within the device 10 and a detailed view of the neck section 110, respectively. As shown, a first end 84 of the measuring strap 80 is received within a pocket 116 formed on the outside surface of the neck section 110 of the device 10. The first end 84 may be seated at any appropriate location. As shown, the end 84 is received within the pocket 116. The strap 80 extends from the pocket 116 into and then through an access channel 118 to a recessed, concave channel 112, which is substantially aligned with the longitudinal axis of the neck section 110 in the illustrated embodiment. The access channel 118 has a width that prevents the end 84 of the measuring strap 80 from passing into/through the access channel 118. That is, the pocket 116 fixedly interconnects or anchors the first end 84 of the strap 80 to the device 10 for tensile loading. Stated another way, the pocket 116 maintains the first end 84 of the strap 80 in a fixed location/position relative to the nose section 110 of the device 10.

The measuring strap 80 extends from the pocket 116 through the access channel 118 to the recessed channel 112, and then through a narrow, concave slot 114 extending through the tip 120 of the device 10. In the illustrated embodiment, the width of the slot 114 is less than the width of the channel 112. The strap 80 forms a loop 82 outside the tip 120 and passes back into and then through the narrow slot 114. In this regard, the narrow slot 114 is sized to allow two opposing portions of the strap 80 to pass through in a sliding relationship while maintaining the strap 80 in an upright position. That is, the narrow slot 114 maintains the narrow edge of the strap 80 in a vertical orientation to facilitate placement of the loop 82 about a patient's tooth. Of note, the slot 14 has a width that allows the two opposing sections of strap 80 to slide relative to each other without significant friction therebetween. The strap 80 continues along the recessed channel 112 to the tensioning mechanism 18 where the second end 86 of the strap 80 is interconnected to or mounted on the reel 30. Each of the pocket 116, the access channel 118, the channel 112, and the slot 114 are concave or open such that they may be accessed on an exterior of the device 10, which facilitates loading of the strap 80 and possibly positioning of the strap 80 about a patient's tooth. When the first end 84 of the measuring strap 80 is disposed within the pocket 116 and the second end 86 of the measuring strap 80 is interconnected to the reel 30 beneath the trigger wheel 20, as will be more fully discussed herein, adjustment of the trigger wheel 20 will expand or contract the loop 82 of the measuring strap 80 beyond the tip 120 of the device 10. In conjunction with expanding/contracting the loop 82, turning of the trigger wheel 20 also moves the indicator needle 40 relative to the graduated gage 60 such that a size of the loop 82 may be determined.

As shown, the tip 120 of the device 10 includes two rounded surfaces 124a and 124b on either side of the narrow slot 114 extending through the tip 120. These generally rounded surfaces 124a–b allow for the opposing portions of the measuring strap 80 to exit the slot 114 in a desired manner that accommodates a variety of tooth configurations/sizes. The opposing portions of the strap 80 may exit the slot 114 substantially aligned with the longitudinal axis of the device 10, or more specifically aligned with the longitudinal extent of the slot 114. Alternatively, the opposing portions of the measuring strap 80 may exit the slot 114 and be disposed at an angle up to substantially perpendicular with the longitudinal axis of the device 10, or more specifically substantially perpendicular to the longitudinal extent of the slot 114. In this regard, it will be appreciated that when the measuring strap 80 is being placed around relatively flat teeth (e.g., incisors) the strap 80 is still then able to at least substantially conform to the tooth and provide accurate circumference measurements. That is, the rounded surfaces 124a–b of the accommodate "spreading" of opposing portions of the strap 80 upon exiting the slot 114 through the tip 120 of the device 10.

Figure 6:
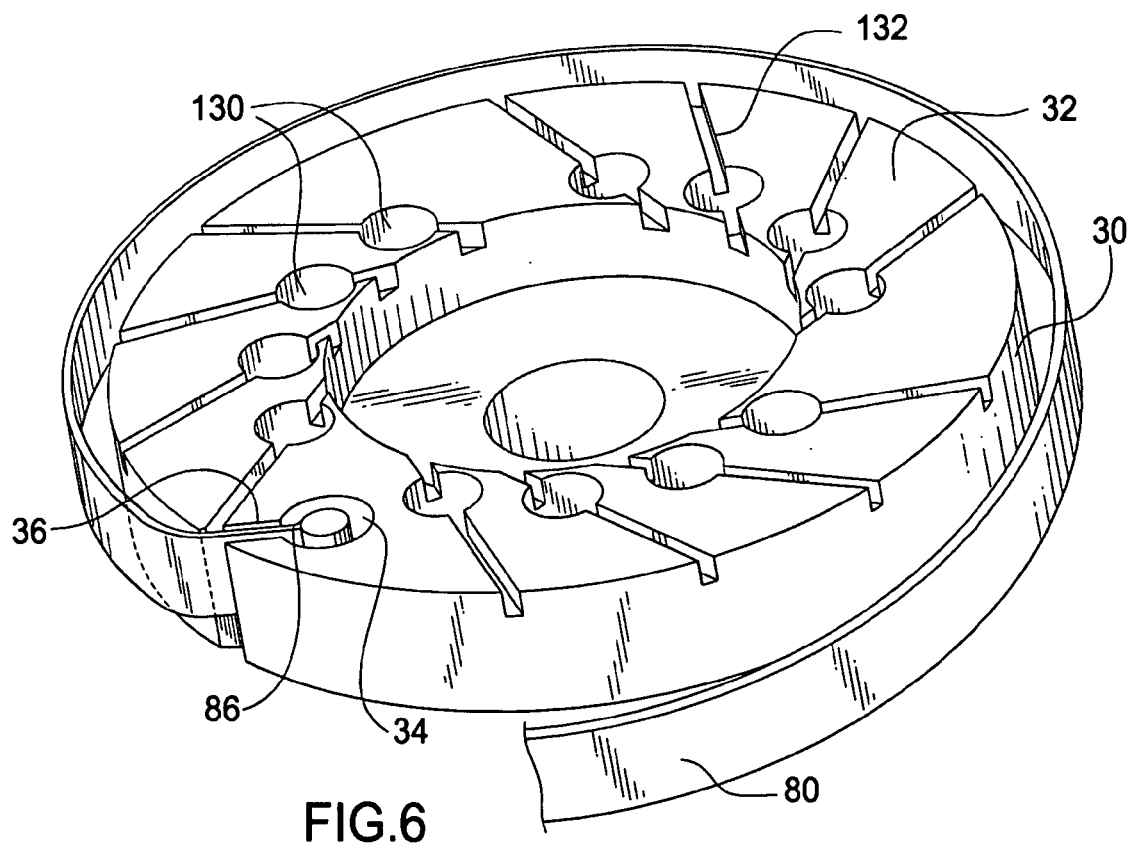

As noted, the second end 86 of the strap 80 is interconnected to the reel 30 of the tensioning mechanism 18 such that the loop 82 extending beyond the tip 120 of the device 10 may be expanded/contracted by turning the trigger wheel 20. As shown in FIG. 6, the second end 86 of the measuring strap 80 is mounted or disposed in a pocket 34 formed in the reel 30. This pocket 34 includes an access channel 36 that extends from the outer perimeter of the reel 30 to the pocket 34 for receipt of the strap 80, and that is sized to prevent the enlarged end 86 of the strap 80 from being able to be pulled back through the access channel 36. In this regard, by turning the reel 30 (e.g., using the trigger wheel 20), a portion of the strap 80 may be wound/unwound about an outside perimeter of the reel 30, thereby adjusting the size of the loop 82 disposed beyond the tip 120 of the device 10.

Affixing one end of the measuring strap 80 to the neck section 110 of the device 10 (end 84) to maintain the same in a stationary position, and adjusting or moving the other end of the strap 80 (end 86), by turning or rotating the trigger wheel 20 and reel 30, allows increased accuracy of tooth measurement to be achieved. That is, fixedly connecting the end 84 of the measuring strap 80 to the device 10 and adjusting the other end 86 of the strap 80 removes one variable that may effect calibrating the gage 60. In any case, by selectively adjusting the tensioning mechanism 18, the size of the loop 82 formed on the end of the measuring strap 80 may be adjusted. In conjunction with adjustment of this loop 82, the indicator needle 40 will move relative to graduation marks 62 on the graduated gage 60, indicating the size of the loop 82 in the measuring strap 80 and therefrom, the circumference of a tooth can be determined.

Figure 7:
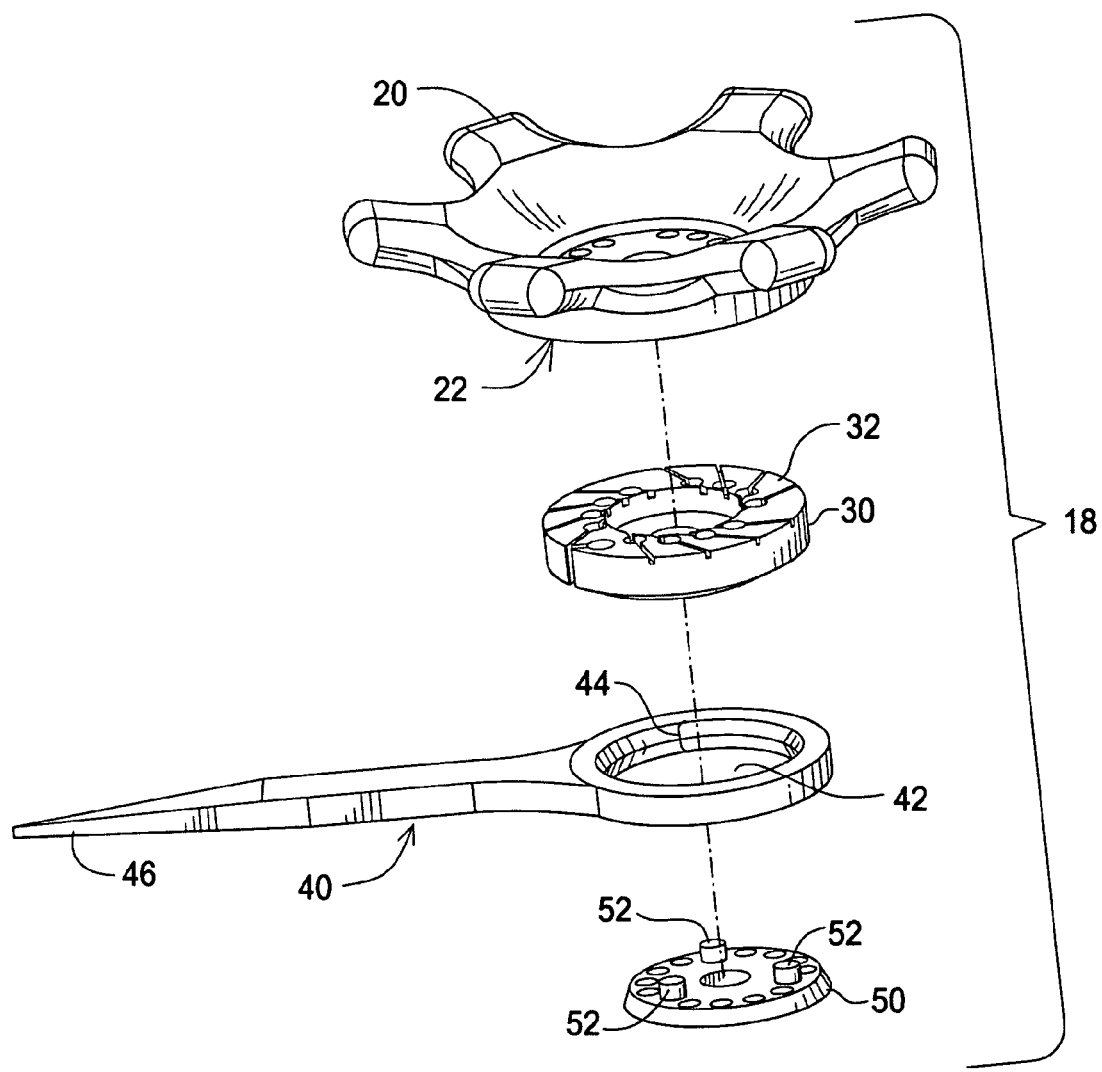
FIG. 7 shows an exploded, perspective view of the tensioning and calibration mechanisms of the tooth circumference-measuring device of FIG. 1.

FIG. 7 shows the components of the tensioning mechanism 18 that turn with the trigger wheel 20 to retract/expand the loop 82 of the measuring strap 80. As previously noted, the tensioning mechanism 18 includes the trigger wheel 20, the reel 30, the indicator needle 40, and a lower needle mandrel 50. When assembled as shown in FIG. 1, the trigger wheel 20 is operative to turn the tensioning mechanism 18 to tighten the measuring strap 80 about a patient's tooth. In this regard, the trigger wheel 20 and the rest of the tensioning mechanism 18 (e.g., reel 30, indicator needle 40 and lower needle mandrel 50) turn as a single unit until a predetermined tension is achieved within the measuring strap 80. Once such a tension is achieved, continued tightening of the trigger wheel 20 will no longer turn the reel 30, the indicator needle 40, and lower needle mandrel 50. In this regard, the tensioning mechanism 18 of the device 10 allows for limiting the amount of tension exerted on a patient's tooth by the measuring strap 80. Accordingly, the same tension may be applied to each tooth such that measurements are consistent from one tooth to the other.

In order to limit the tension applied to a patient's tooth via the strap 80, the trigger wheel 20 and reel 30 are mounted in a frictional relationship. That is, a top friction surface 32 of the reel 30 engages a bottom friction surface 22 of the trigger wheel 20. This frictional interface between the trigger wheel 20 and reel 30 allows the two members to be turned as a unit until the tension within the measuring strap 80 is greater than the frictional force between the faces 22 and 32 of the trigger wheel 20 and reel 30. That is, the trigger wheel 20 and reel 30 turn as a unit until the tension within the measuring strap 80 overcomes the frictional force between these members 20, 30, which is determined by the normal compressive force exerted by the bolt 12 and washers 16, the surface area of the surfaces 22 and 32, and the coefficient of friction of these surfaces 22 and 32. In practice, this allows a user to selectively tighten the wing nut 14 to achieve a desired frictional force between the trigger wheel 20 and reel 30. In any case, once the predetermined tension is achieved within the measuring strap 80, the frictional force between the trigger wheel 20 and reel 30 is overcome and the trigger wheel 20 turns free of the reel 30. That is, although the trigger wheel 20 may continue to rotate, the reel 30 will remain stationary. As will be appreciated, when the trigger wheel 20 turns free of the reel 30, the measuring strap 80 is not further tensioned and the indicator needle 40 no longer moves. Stated another way, once the trigger wheel 20 rotates relative to the reel 30, the size of the loop 82 of the strap 80 does not change such that the band size may be read from the gage 60 via the indicator needle 40.

In order to move the indicator needle 40 relative to the gage 60, the reel 30 and the lower needle mandrel 50 are designed to fixedly interface with one another such that the indicator needle 40 is trapped therebetween. In this regard, the lower needle mandrel 50 includes three equally spaced bosses 52 that are received within corresponding apertures 56 on the bottom surface of the reel 30 (FIG. 8). When so engaged, the reel 30 and lower needle mandrel 50 trap the indicator needle 40 and turn as a single unit. FIG. 8a shows a cross-sectional view taken along the longitudinal axis of the device 10 of the reel 30 engaged with the lower needle mandrel 50 and the trapped indicator needle 40. However, any way of registering the lower needle mandrel 50 relative to the reel 30 may be utilized.

Though trapped between the reel 30 and the lower needle mandrel 50, the indicator needle 40 is not fixedly interconnected to either of these components. The indicator needle 40 can move relative to both the reel 30 and the lower needle mandrel 50 in at least certain circumstances, for instance during calibration. Specifically, the indicator needle 40 is trapped in a frictional relationship between these components, 30, 50 such that the indicator needle 40 may be adjusted for calibration purposes, as will be discussed herein. As shown in FIGS. 8 and 8a, a central aperture 42 of the indicator needle 40 is sized to fit around a land 38 raised on the bottom surface of the reel 30, as well as around a portion of the outside surface 54 of the lower needle mandrel 50. In the embodiment shown, the land 38 on the bottom surface of the reel 30 is tapered, as is the outside surface 54 of the lower needle mandrel 50. In this regard, when disposed in a mating relationship, the outer surface of the land 38 and outside surface 54 of the lower needle mandrel 50 collectively define a concave surface having an included angle θ of about 150°. Accordingly, the interior surface of the central aperture 42 of the needle indicator 40 forms a mating pyramidal edge 44 (i.e., convex surface) that substantially matches the concave surface formed by the bottom land 38 and lower needle mandrel 50. The mating relationship of the convex pyramidal edge 44 of the indicator needle 40 with the concave surface formed by the land 38 and lower needle mandrel 50 substantially prevents axial movement (i.e., in a direction aligned with the bolt 12 as shown in FIG. 2) of the indicator needle 40 upon assembly of the device 10. When the device 10 is assembled, a top surface of the pyramidal edge 44 of the indicator needle 40 is in an annularly co-planar relationship with the outside surface of the land 38 and the bottom surface of the pyramidal edge 44 of the indicator needle 40 is in an annularly co-planar relationship with the outside surface 54 of the lower needle mandrel 50. In this regard, the indicator needle 40 is in a frictional relationship with the interconnected reel 30 and lower needle mandrel 50. Accordingly, the indicator needle 40 will turn with the reel 30 and lower mandrel 50 until the frictional force between these members is overcome. The use of the frictional relationship allows a user to adjust the pointer 46 of the indicator needle 40 (i.e., move the needle 40 free of the reel 30 or without rotating the reel 30) to a predetermined graduation mark 62 on the gage 60. This may be done while the loop 82 is disposed around a standard of a known circumference such that the device 10 may be calibrated.

Though the tensioning mechanism 18 is operative to rotate about the bolt 12 to adjust the measuring strap 80, the graduated gage 60 remains fixedly interconnected to the device 10 (i.e., remains stationary) during tooth measurement. However, as will be appreciated by those skilled in the art, orthodontic bands come in a variety of sizes, which may be characterized differently by different manufacturing entities. In this regard, orthodontic bands from different entities may utilize different measuring units. Accordingly, it may be desirable to have a plurality of different graduated gages 60 for use when fitting orthodontic bands from different band manufacturers. In this regard, while being fixedly interconnected to the device 10 during measurement, it may be desirable for the graduated gage 60 to be removable such that many of a plurality of selectable graduated gages 60 may be utilized. Multiple gages 60 may also be desirable to accommodate different classes of teeth, as well as for use in sizing dental hardware such as temporary pedodontic crowns and other tooth accommodating orthodontic armamentarium.

Figure 9:
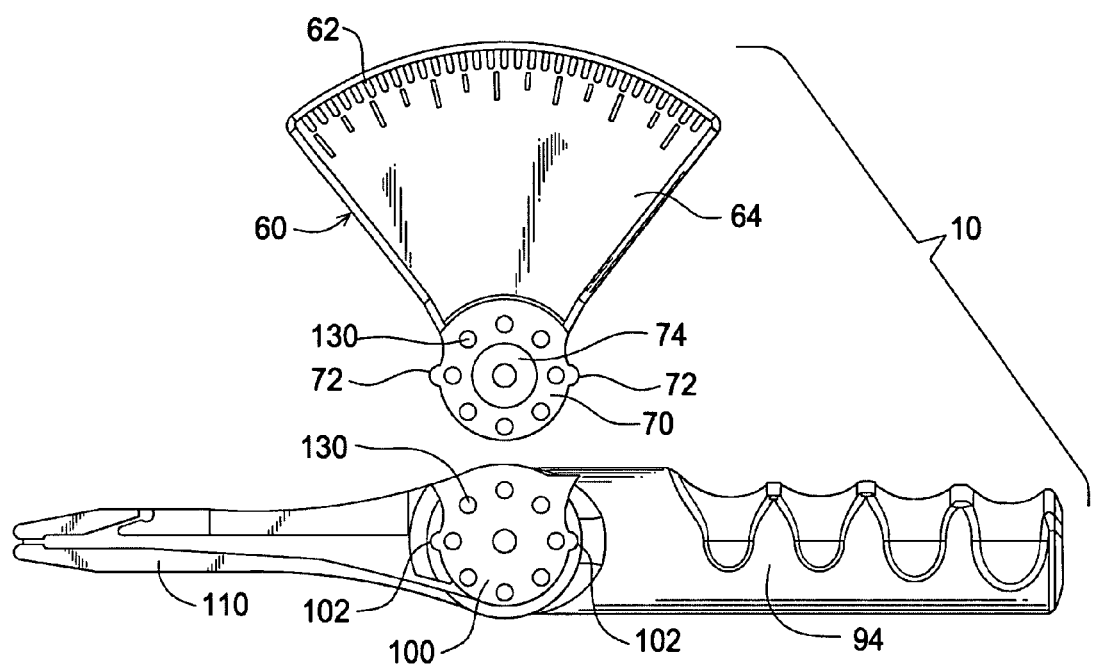
FIG. 9 shows a plan view of the gage and handle of the tooth circumference measuring device of FIG. 1, prior to installation of the gage.

As shown in FIG. 9, the graduated gage 60 is received on the bottom surface of the socket 100. In this regard, a hub end 70 of the graduated gage 60 is disposable within the socket 100. In order to be fixed relative to the device 10 during tooth measurement, the hub end 70 includes first and second ears 72 on opposing sides. These ears 72 engage mating indentions 102 formed on the side surfaces of the socket 100. In this regard, upon assembly of the device 10, the graduated gage 60 is fixedly interconnected within the socket 100. Any way of registering the gage 60 relative to the socket 100 may be utilized.

Referring again to FIG. 9, it will be noted that the graduated gage 60 is substantially fan-shaped opposite the hub end 70. The fan end 64 of the gage spans an arc of about 75° on which the graduations 62 are evenly marked. As will be appreciated, the pointer 46 of the indicator needle 40 moves through this arc in conjunction with the turning of the trigger wheel 20 during tightening of the measuring strap 80 about a patient's tooth. Accordingly, the outside diameter of the reel 30 in effect dictates the graduation of the marks 62 on the fan end 64 of the gage 60. That is, rotation of the reel 30 by a given amount (e.g., 20°) will result in a portion of the measuring strap 80 being wound about the outside perimeter of the reel 30. Accordingly, a bigger reel 30 will result in more of the measuring strap 80 being retracted than will a smaller diameter reel 30 for a given amount of rotation. In any case, the graduation marks 62 are set to correspond to a reel 30 of a known diameter. Furthermore, the reel 30 is sized such that a 75° sweep of the gage 60 will match or exceed the statistical range of all tooth sizes likely to be measured with the gage 60. Separate gages 60 may be utilized for molars, bicuspids, and incisors.

Referring to FIGS. 2 and 9, it will be noted that the tensioning mechanism 18, including the trigger wheel 20, reel 30, indicator needle 40, and lower needle mandrel 50, are assembled on top of the hub end 70 of the gage 60. As will be appreciated, friction between the bottom surface of the lower needle mandrel 50 and the top of the hub end 70 of the gage 60 could alter the frictional relationship between the trigger wheel 20 and reel 30. That is, additional friction could result in less consistent frictional release between the trigger wheel 20 and reel 30. In order to minimize the friction between the gage 60 and lower needle mandrel 50, the tensioning mechanism 18 rides on top of a raised land 74 on the hub 70. In this regard, there is a reduced surface area and correspondingly reduced frictional force between the hub 70 and the bottom surface of the lower needle mandrel 50. Furthermore, to better isolate the tension between the bottom surface 22 of the trigger wheel 20 and the top surface 32 of the reel 30, the interface between the lower needle mandrel 50 and the top of the land 74 may be lubricated utilizing, for example, a glycerin, a silicone grease or other preferably non-petroleum based lubricants.

The device 10 may be made out of any suitable material that provides desired rigidity to withstand forces applied during tooth measurement. Furthermore, some components (e.g. the tensioning mechanism 18 and handle 94) may be made of different materials. In one embodiment, the handle 94 and nose section 110 are of a one-piece construction, and each of the tension wheel 20, the reel 30, indicator needle 40, lower needle mandrel 50, and gage 60 are separate parts (e.g., each being injection molded and/or machined). However, in one preferred embodiment the device 10 the separate components are formed of injection moldable material (e.g., a polymer) to reduce the cost of the resulting device 10. Regardless of the material utilized, it will be appreciated that, for sterilization purposes, it may be desirable for the device 10 to be able to withstand elevated temperatures. For example, heat sterilization may require the device 10 to withstand temperatures of up to 400° F. for six or seven minutes. Alternatively, autoclave sterilization may require the device 10 to withstand temperatures of up to 260–280° F. at an elevated pressure. For example, the device 10 may utilize a polysulfone polymer. Other suitable polymers may be used as well as polymers modified with reinforcing additives such as glass fibers.

Alternatively or in addition to being able to be heat sterilized, the device 10 may be made such that it can be sterilized using cold sterilization methods. That is, the device 10 may be formed such that it may be immersed within a sterilization bath for sterilization purposes. One problem associated with cold sterilization of medical devices is the trapping of sterilant within the device. In this regard, the illustrated device 10 has multiple drain holes 130 and drain channels 132 formed on its various components that allow cold sterilant to be evacuated and rinsed from the device 10 on removal from a sterilant bath. Referring generally to FIGS. 1, 2, 4, 6, 7 and 9, it will be noted that these drainage holes 130 extend through each of the axially aligned components, as well as through the bottom surface of the socket 100. Furthermore, as best shown in FIG. 6, the top surface 32 of the reel 30 includes a number of drainage channels 132 that allow sterilant to exit what may otherwise be an enclosed interior volume upon assembly.

For additional sterilization purposes, the device 10 is designed such that the measuring strap 80 may be easily replaced between usages on different patients. For example, the wing nut 14, and conical washers 16 may be removed from the bolt 12 to allow for the trigger wheel 20 to be removed from the reel 30. As will be appreciated, this exposes the second end 86 of the measuring strap 80. Accordingly, the first end 84 of the measuring strap may be removed from the pocket 116 within the neck section 110 of the device 10 and the second end 86 of the measuring strap 80 may be removed from the pocket 34 within the reel 30. A different measuring strap 80 may then be disposed therein or loaded, and the trigger wheel 20 reassembled on top of the reel 30.

Prior to making circumference measurements of a patient's tooth, the device 10 should be calibrated. In this regard, the loop 82 extending past the tip 120 of the device 10 may be placed around an element of a known circumference or standard. That is, the loop 82 of the measuring strap 80 may be placed around a standard and the tensioning mechanism 18 may be tightened until the trigger wheel 20 rotates free of the reel 30. At this time, the indicator needle 40, which is held in a frictional relationship between the reel 30 and the lower needle mandrel 50, may be forcibly moved relative to both the reel 30 and lower needle mandrel 50 to a graduation on the gage 60 corresponding to a value corresponding with the known circumference of the standard. For example, if the standard has a circumference of 3 cm, upon properly tensioning the measuring strap 80, the indicator needle 40 would be moved to a 3 cm graduation 62 on the gage 60. After calibration, the standard is removed and measurements may be taken of a patient's teeth. As will be appreciated, so long as the needle 40 is not disturbed (i.e., is only moved as a unit with the reel 30 and lower needle mandrel 50), measurements of multiple teeth may be taken without recalibration.

Figure 10:
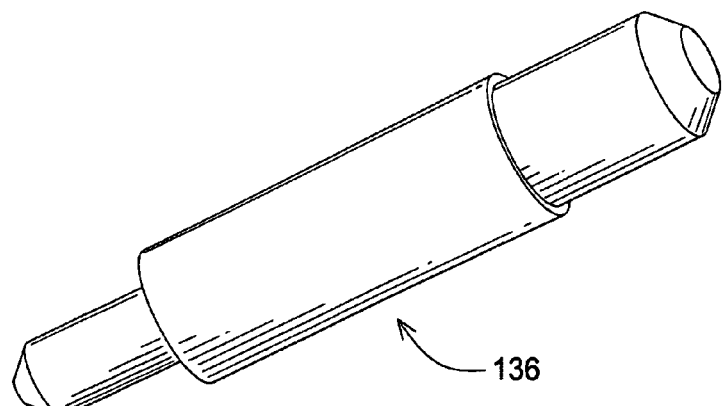
FIG. 10 shows a perspective view of a standard that may be utilized to calibrate the tooth circumference measuring device of FIG. 1.

As noted above, different classes of teeth (e.g., molars, cuspids) may require the use of different calibration gages 60. Accordingly, each gage 60 may have to be separately calibrated. In this regard, separate standards may be required for each graduated gage 60. FIG. 10 shows a standard 136 may be utilized with a plurality of different gages 60. As shown, the standard 136 includes three substantially cylindrical sections. Of note, using the device 10 with a different gage 60 and/or standard 136, may also require the use of a differently sized reel 30 and/or strap 80.

Each of these sections may correspond to a different gage 60 that may be utilized for measuring different classes of teeth, such as cuspids, bicuspids, and molars. In one preferred embodiment, the standard 136 will fit within a recess 180 located through the end of the handle 94 such that standard 136 may be kept with the device 10. See FIG. 1.

Once the device 10 is calibrated, measurement of a patient's teeth for orthodontic fitting may be performed. Measurement requires placement of the loop 82 around a tooth, tensioning of the measuring strap 80 by turning the trigger wheel 20 (preferably until the trigger wheel 20 frictionally releases from the reel 30), and reading the graduation mark 62 indicated by the pointer 46 of the needle indicator 40. This process may be repeated for each tooth to be measured. One difficulty that may arise, especially with the rearward teeth, is placement of the loop 82 around each individual tooth. In this regard, the trigger wheel 20 may be turned to expand the loop 82 to a maximum size. However, this may still result in a loop 82 that is does not provide enough slack to facilitate placement of the loop 82 around the tooth. In this regard, the open recessed channel 112 of the neck section 110 provides an important benefit. Namely, the open recessed channel 112 allows removal of the measuring strap 80 between measurements. That is, to provide extra slack the measuring strap 80 may be removed from the narrow slot 114 on the tip 120 of the device 10, as well as from all or a portion of the recessed channel 112. Furthermore, if necessary, the end 84 of the measurement strap 80 may also be removed from the pocket 116 to provide additional flexibility in measurement loop 82 placements. In this regard, more of the measurement strap 80 may be made available for initial placement around a patient's tooth. Once positioned about the tooth, the measurement strap 80 may be reengaged into the narrow slot 114/recessed channel 112 and/or the pocket 116 such that a calibrated circumference measurement may be made. As will be appreciated, so long as the indicator needle 40 is not disturbed during this process, the device 10 will remain calibrated, notwithstanding removal a portion of the measurement strap 80 from the neck section 110 of the device 10.

Figure 11:
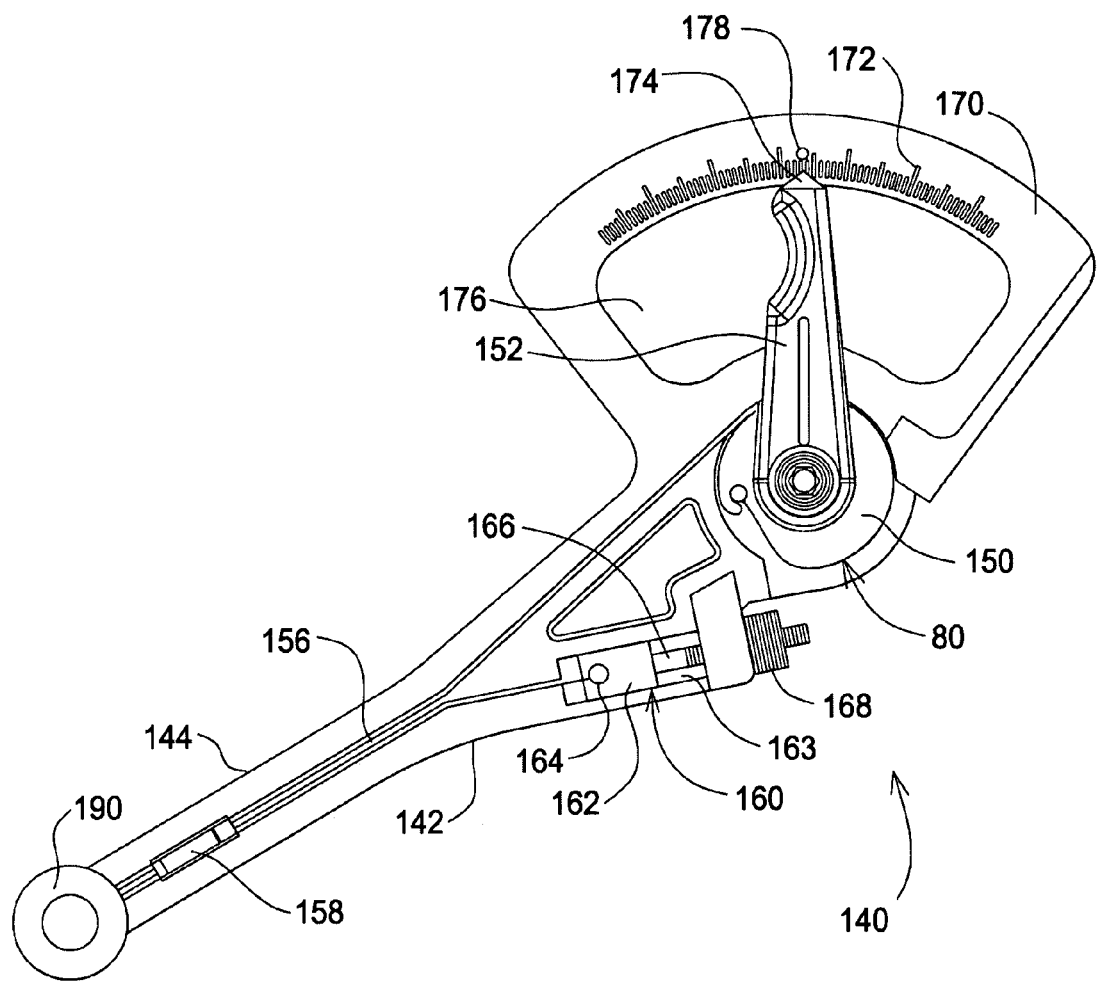
FIG. 11 shows a top view of a second embodiment of a tooth circumference measuring device.
Figure 12:
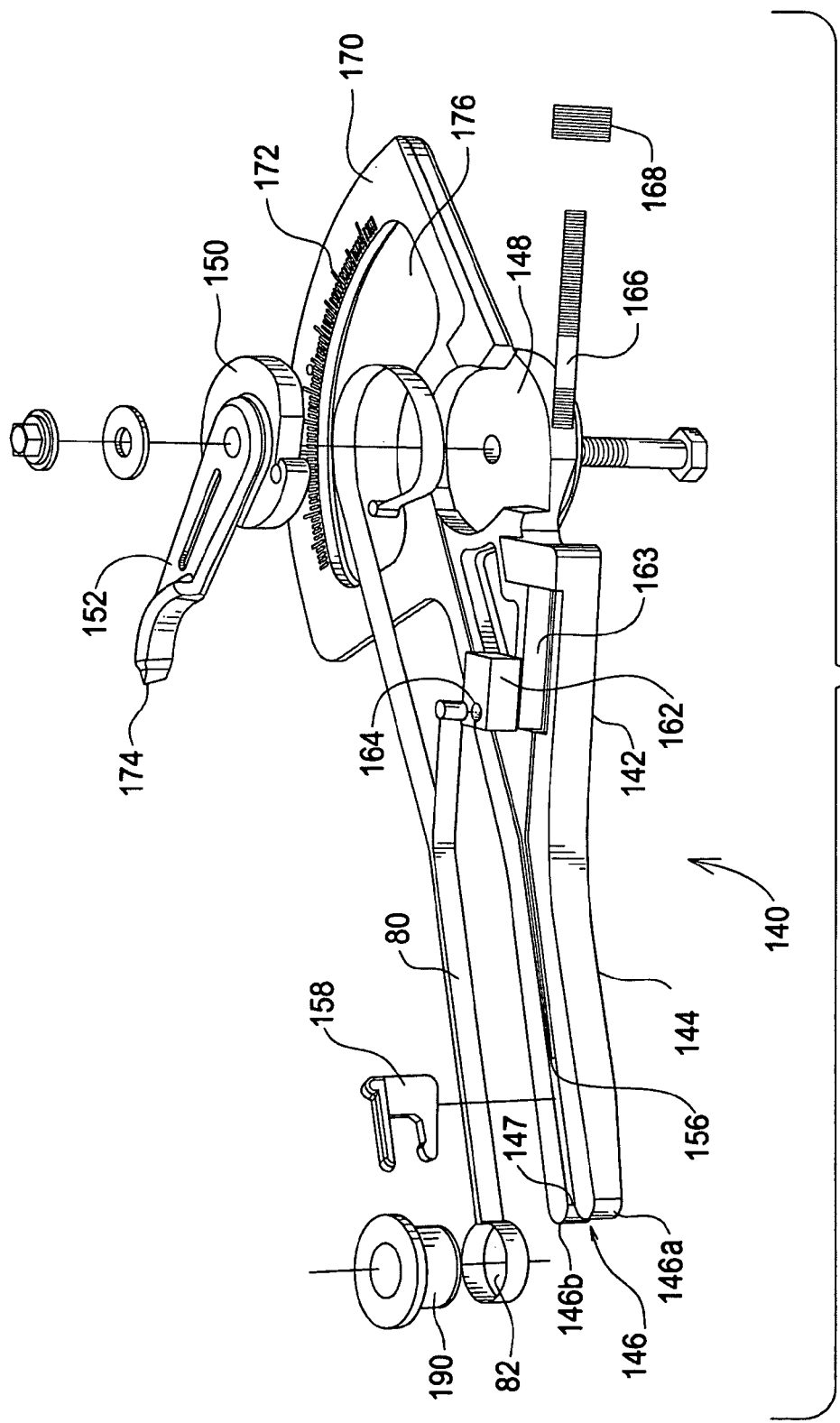
FIG. 12 shows an exploded perspective view of the device of FIG. 11.

FIGS. 11 and 12 show a second embodiment of a tooth circumference measuring device 140 that shares many of the characteristics disclosed in relation to the embodiment discussed herein above. Though similar in many aspects, the second embodiment of the device 140 does not utilize the limited tension tensioning mechanism 18. As shown, the device 140 includes a body 142 having an elongated neck section 144 terminating in a tip 146, which is disposable within a patient's mouth. Again a measuring strap 80 protrudes from the tip 146 of the device 140 to form a loop 82 for placement around a patient's tooth. The loop 82 may be expanded or contracted by turning a reel 150 that is rotatably coupled to the body 142. As shown, the reel 150 is located within a socket 148 within the body 142 and a lever 152 is fixedly interconnected to the reel 150. Accordingly, the lever 152 is utilized to rotate the reel 150. The reel 150 is substantially similar to the reel as shown in relation to the embodiment of FIG. 1. Again, the reel 150 incorporates a pocket for use in trapping a mandrel on a first end of the measuring strap 80.

The strap 80 is disposed around a portion of the outside perimeter of the reel 150 such that when the reel 150 is rotated, the strap 80 is wound or unwound around the reel 150. The strap 80 extends from the reel 150, through a channel 156, through the tip 146 of the device 140 to form the loop 82, and is redirected back through the tip 146 and is anchored to a calibration device 160. As in the embodiment of FIG. 1, the tip 146 includes a slot 147 that is sized to allow two opposing portions of the strap 80 to pass through in a sliding relationship, while maintaining the strap 80 in an upright position. Again, the tip 146 may include two rounded surfaces 146a and 146b that allow for opposing portions of the measuring strap 80 to exit the slot 147 in a desired manner that accommodates a variety of tooth configurations and/or sizes.

A gage 170 is interconnected to a rearward end of the body 142. Again, the gage 170 is a fan-shaped radial gage and includes a plurality of evenly spaced graduations 172. The gage 170 may include a replaceable faceplate or, the gage 170 may itself be removeably interconnected to the body 142 such that a variety of different gages 170 having different graduations may be utilized. In the embodiment of FIGS. 11 and 12, the lever 152 utilized to turn the reel 150 also forms the indicator for the gage 170. Any structure that both moves the reel 150 and cooperates with the gage 170 for indicating sizing may be utilized. In this regard, the lever 152 further includes a pointer 174 that moves along the graduations 172 as the lever 152 turns the reel 150, and hence contracts or expands the loop 82 through the tip 146 of the device 140. That is, the pointer 174 moves through the arc defined by the gage 170 in conjunction with expanding or contracting the measuring loop 82 about a patient's tooth.

As shown, the gage 170 further includes an aperture 176 that allows a technician to grasp the lever 152 for tensioning purposes. In particular, the lever 152 forms a trigger, allowing a technician to pull the lever 152 using a single finger and thereby rotating the reel 150 and tightening the loop 82 about a patient's tooth. Once the desired tension is achieved about the tooth, the technician may read the size off the gage 170.

The calibration device 160 allows for conveniently calibrating the tooth measuring device 140. In this regard, a standard 190 having a known circumference is again placed within the loop 82. A first end of the measuring strap 80 interconnected to the reel 150 is then rotated to a desired position. More particularly, the lever 152 is rotated to a calibration point 178 on the gage 170. The lever 152 is then held at this calibration point 178 while the calibration device 160 is adjusted to achieve a desired tension in the strap 80 about the standard 190. As will be appreciated, calibration may also require loosening of the calibration device 160 to allow the lever 152 to be positioned relative to the calibration point 178. Preferably, a technician utilizing the device 140 will adjust the calibration device 160 to achieve a desired tension in the strap 80 during calibration and then attempt to duplicate that tension when a patient's tooth is disposed within the loop 82 to achieve an accurately calibrated measurement.

The calibration adjuster 160 includes an anchor block 162 that has a pocket 164 for receiving a second end of the measuring strap 80 in a manner similar to that discussed above. The anchor block 162 is slidably disposed within a trough 163 within the body 142 that allows the block 162 to move forward and backward while preventing the anchor block 162 from rotating. A bolt 166 is threaded into a rearward end of the anchor block 162 and extends through a back wall of the trough 163. A nut 168 is threaded onto the bolt 166 extending through the trough 163. The nut 168 is utilized to move the anchor block 162 forward and rearward in order to tension or slacken the measuring strap 80 for calibration purposes. That is, the calibration adjuster 160 changes the position of the second end of the strap 80 relative to the body 142.

Figure 13:
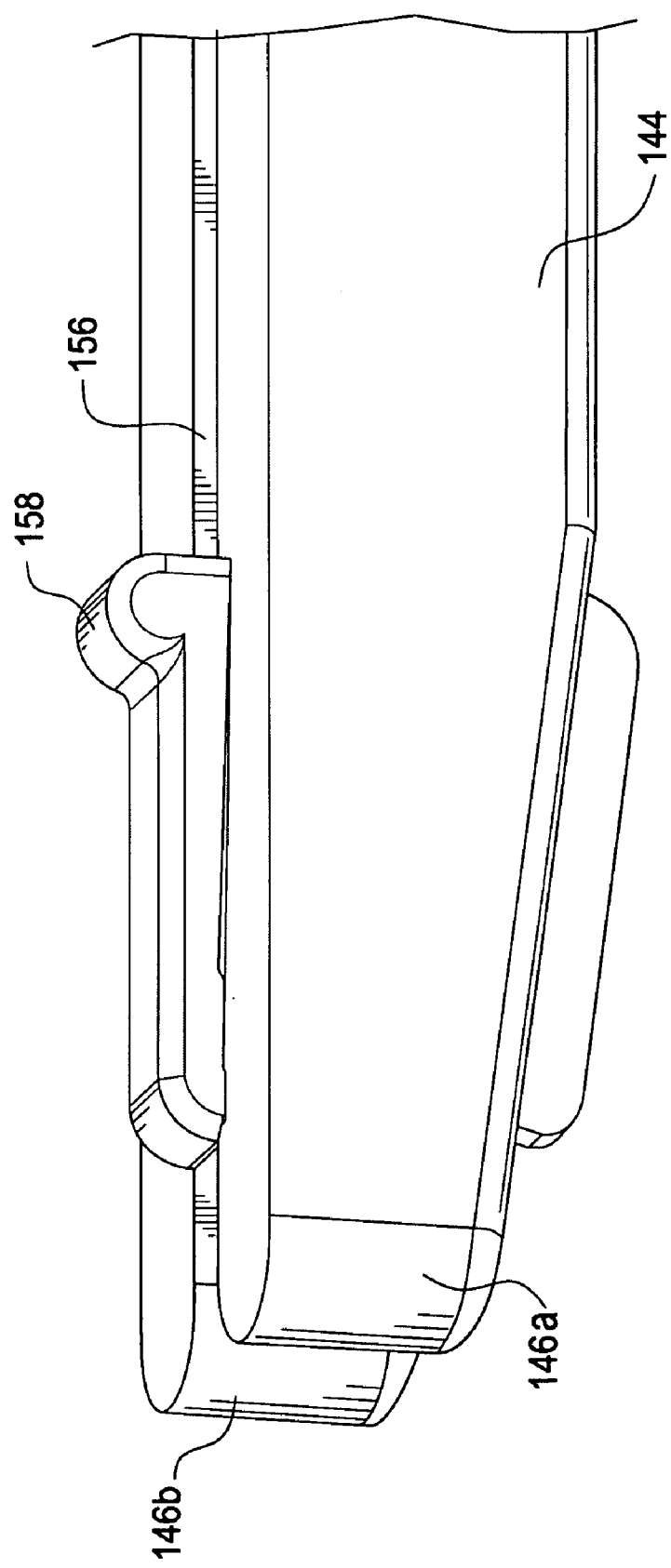
FIG. 13 shows a close up perspective view of the forward end of the device of FIG. 11.

As shown in FIGS. 11–13, the second embodiment 140 further includes a clip 158 interconnected on the neck section 144 of the device 140 near the tip 146 for maintaining the strap 80 within the channel 156. In the embodiment shown, the clip 158 is formed of a U-shaped member that extends through the neck section 144 of the device 140. Once disposed through the neck section 144, the U-shaped clip member 158 is slid forward such that each leg of the U engages an outside surface of the neck section 144. Importantly, the top leg section is sized to fit over the channel 156 such that the strap 80 is trapped therein. However, it will be appreciated that any means for maintaining the strap within the channel 156 may be utilized.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. For instance, measuring straps 80 having different lengths may be utilized when gages are replaced with the device 140 such that teeth of different classes may be measured. Likewise, different standards may be utilized for calibrating differently sized measuring straps. The embodiments described hereinabove are further intended to explain best modes known of practicing the invention and to enable others skilled in the art to utilize the invention in such, or other embodiments and with various modifications required by the particular application(s) or use(s) of the present invention.

The invention claimed is:

1. A device for measuring the circumference of a tooth, comprising:
    a body comprising a tip section;
    a reel rotatively coupled to said body;
    a measuring strap comprising a first portion anchored to and rotatable with said reel, a second portion anchored to said body, and a loop disposed beyond said tip section, wherein said measuring strap may be wound and unwound about at least a portion of a perimeter of said reel to adjust a size of said loop;
    a gage associated with said body;
    an elongated lever having a first end interconnected to said reel and having a second end extending beyond said perimeter of said reel, said lever being operative to rotate said reel in conjunction with said elongated lever moving over a surface of said gage, wherein a force applied to said lever moves said lever and applies a force to said measuring strap; and a calibrator comprising a first section interconnected with said second portion of said measuring strap and movable relative to said body so as to change a position of said second portion of said measuring strap relative to said body.

2. The device of claim 1, further comprising:
an indicator associated with said elongated lever, wherein a position of said indicator relative to said surface of said gage is indicative of a size of said loop.

3. The device of claim 2, wherein said gage is removeably attached to said body.

4. The device of claim 2, wherein said indicator is disposed on said second end of said elongated lever.

5. The device of claim 1, wherein said first and second portions are removeably anchored to said reel and said body, respectively.

6. The device of claim 1, further comprising:
a concave channel formed on an exterior surface of said body and extending from said reel through said tip section, wherein said measuring strap is disposed within said channel.

7. A device for measuring the circumference of a tooth, comprising:
a body comprising a tip section;
a measuring strap comprising a loop disposed beyond said tip section;
a lever movably coupled to said body about an axis, wherein said measuring strap is operatively interconnected to said lever at a first distance from said axis;
an indicator associated with said lever at a second distance from said axis, wherein said second distance is greater than said first distance; and
a gage having a plurality of spaced gradations, wherein a position of said indicator relative to said spaced gradations on said gage is indicative of a size of said loop and wherein said lever extends over an aperture that is located between said axis and said gage that accommodates a gripping of said lever for actuation.

8. The device of claim 7, further comprising:
a reel rotatively coupled to said lever, wherein at least a first portion of said measuring strap is anchored to and rotatable with said reel.

9. The device of claim 7, wherein said gage comprises said aperture.

10. The device of claim 7, wherein said gage is removeably attached to said body.

11. The device of claim 7, wherein said measuring strap is removeably attached to said device.

12. The device of claim 7, further comprising:
an adjustor operative to move a first portion of said strap so as to change a position of said lever.

13. A device for measuring the circumference of a tooth, comprising:
a body comprising a tip section;
an adjusting mechanism movably interconnected to said body;
a concave channel formed on an exterior surface of said body and extending from said adjusting mechanism through said tip section; and
a measuring strap disposed within said channel and comprising a first portion interconnected to said adjusting mechanism, a second portion anchored to said body, and a loop disposed beyond said tip section.

14. The device of claim 13, further comprising:
a gage attached to said body; and
an indicator operative to move with said strap, wherein a position of said indicator relative to said gage is indicative of a size of said loop.

15. The device of claim 13, wherein said channel is sized to maintain said strap in an upright position.

16. The device of claim 15, wherein said channel has a substantially U-shaped cross-section.

17. The device of claim 13, wherein said adjusting mechanism is rotatively interconnected to said body.

18. The device of claim 17, wherein said adjusting mechanism comprises a reel and wherein said first portion of said strap is anchored to and rotatable with said reel.

19. A device for measuring the circumference of a toot, comprising:
a body comprising a tip section;
a reel rotatively coupled to said body;
a measuring strap comprising a first portion anchored to said reel, a second portion anchored to said body, and a loop disposed beyond said tip section; and
a strap adjuster mounted on said reel, wherein a frictional interface between said strap adjuster and said reel allows said reel to rotate along with said strap adjuster when a force being exerted on said reel by said measuring strap is less than a certain amount, and wherein said reel remains stationary during rotation of said strap adjuster when a force being exerted on said reel by said measuring step is greater than said certain amount.

20. The device of claim 19, further comprising:
a gage attached to said body; and
an indicator operative to rotate with said reel, wherein a position of said indicator relative to said gage is indicative of a size of said loop.

21. The device of claim 20, wherein said gage is removeably attached to said body.

22. The device of claim 20, wherein said first and second portions are removeably anchored to said reel and said body, respectively.

23. The device of claim 19, further comprising:
an adjustable fastener for mounting said strap adjuster to said reel, wherein said fastener allows for selectively adjusting a compression force between said strap adjuster and said reel.

24. A device for measuring the circumference of a tooth, comprising:
a body comprising a tip section;
a measuring strap comprising a first portion, a second portion, and a loop disposed beyond said tip section and located between said first and second portions;
a strap adjuster movable relative to said body and interconnected with said first portion of said measuring strap; and
a calibrator comprising a first section interconnected with said second portion of said measuring strap and movable relative to said body so as to change a position of said second portion of said measuring strap.

25. The device of claim 24, further comprising:
a gage attached to said body; and
an indicator operative to move with said strap, wherein a position of said indicator relative to said gage is indicative of a size of said loop.

26. The device of claim 25, wherein said gage is removeably attached to said body.

27. The device of claim 24, wherein said first and second portions of said strap are removeably anchored to said adjuster and said calibrator, respectively.

28. The device of claim 24, wherein said strap adjustor comprises a reel and wherein said first portion of said strap is anchored to and rotatable with said reel.

29. The device of claim 28, wherein strap adjustor further comprises a lever interconnected to said reel.

30. A device for measuring the circumference of a tooth, comprising:
- a body comprising a tip section;
- a slot that extends to an end of said tip section, wherein said end of said tip section comprises first and second rounded surfaces disposed on opposite sides of said slot;
- an adjusting mechanism interconnected to said body;
- a measuring strap comprising a first portion interconnected to said adjusting mechanism, a second portion anchored to said body, and a loop disposed beyond said tip section, wherein said measuring loop is disposed within said slot; and
- wherein said slot comprises a concave channel formed on an exterior surface of said body and extending from said adjusting mechanism to said end of said tip section.

31. The device of claim 30, wherein said adjusting mechanism comprises an elongated lever movably coupled to said body about an axis.

32. The device of claim 31, wherein said second portion of said measuring strap is interconnected to said elongated lever at a location between said axis and an end of said elongated lever.

33. The device of claim 30, wherein said adjustor mechanism further comprises
- a reel for wherein said measuring strap may be wound and unwound about at least a portion of a perimeter of said reel and wherein a frictional interface between said reel and a strap adjustor of said adjustor mechanism allows said reel to rotate along with said strap adjustor when a force being exerted on said reel by said measuring strap is less than a certain amount, and wherein said reel remains stationary during rotation of said strap adjuster when a force being exerted on said reel by said measuring step is greater than said certain amount.

* * * * *

UNITED STATES PATENT AND TRADEMARK OFFICE
CERTIFICATE OF CORRECTION

| | | |
|---|---|---|
| PATENT NO. | : 7,047,656 B1 | Page 1 of 1 |
| APPLICATION NO. | : 10/835126 | |
| DATED | : May 23, 2006 | |
| INVENTOR(S) | : Parker | |

It is certified that error appears in the above-identified patent and that said Letters Patent is hereby corrected as shown below:

<u>Column 18</u>
Line 15, delete "toot" and insert therefor --tooth--.

Signed and Sealed this

Twenty-second Day of August, 2006

JON W. DUDAS
*Director of the United States Patent and Trademark Office*